United States Patent [19]
Wolter et al.

[11] Patent Number: 5,323,936
[45] Date of Patent: Jun. 28, 1994

[54] MEDIA DISPENSER FOR DISPENSING A DOSED MEDIUM IN A GAS FLOW

[75] Inventors: Michael Wolter, Steckborn, Switzerland; Friedrich Zuckschwerdt, Radolfzell, Fed. Rep. of Germany

[73] Assignee: Ing. Erich Pfeiffer GmbH & Co. KG, Fed. Rep. of Germany

[21] Appl. No.: 74,768

[22] Filed: Jun. 10, 1993

Related U.S. Application Data

[63] Continuation of Ser. No. 752,839, Aug. 30, 1991, abandoned.

[30] Foreign Application Priority Data

Sep. 1, 1990 [DE] Fed. Rep. of Germany ....... 4027749

[51] Int. Cl.$^5$ ............................................. B65D 83/06
[52] U.S. Cl. ................................. 222/401; 222/631
[58] Field of Search ............... 222/209, 354, 385, 401, 222/402, 630, 631; 239/369

[56] References Cited

U.S. PATENT DOCUMENTS

| | | | |
|---|---|---|---|
| 1,552,181 | 9/1925 | Solomon et al. | 604/58 |
| 2,581,182 | 1/1952 | Fields | 128/206 |
| 2,591,962 | 4/1952 | Nachbar | 299/88 |
| 2,974,879 | 3/1961 | Raehs et al. | 239/357 |
| 3,162,332 | 12/1964 | Hayim | 222/193 |
| 3,240,396 | 3/1966 | Friedenberg | 222/146 |
| 3,323,689 | 6/1967 | Elmore | 222/385 |
| 3,360,168 | 12/1967 | Bret | 222/335 |
| 3,900,138 | 8/1975 | Phillips | 222/340 |
| 4,113,147 | 9/1978 | Frazier et al. | 222/131 |
| 4,214,677 | 7/1980 | Bauer et al. | 222/145 |
| 4,310,104 | 1/1982 | Takatsuki | 222/131 |
| 4,531,660 | 7/1985 | Ford, Jr. | 222/209 |
| 4,550,864 | 11/1985 | Tarozzi et al. | 222/206 |
| 4,570,630 | 2/1986 | Elliott et al. | 128/203.15 |
| 5,048,750 | 9/1991 | Tobler | 222/189 |
| 5,156,307 | 10/1992 | Callahan et al. | 222/189 |
| 5,219,102 | 6/1993 | Wright | 222/190 |

FOREIGN PATENT DOCUMENTS

| | | |
|---|---|---|
| 309010 | 3/1989 | European Pat. Off. . |
| 872253 | 3/1956 | Fed. Rep. of Germany . |
| 1016198 | 9/1957 | Fed. Rep. of Germany . |
| 1201684 | 9/1965 | Fed. Rep. of Germany . |
| 2337220 | 2/1975 | Fed. Rep. of Germany . |
| 343819 | 6/1978 | Fed. Rep. of Germany . |
| 2830677 | 1/1979 | Fed. Rep. of Germany . |
| 3811309 | 10/1989 | Fed. Rep. of Germany . |
| WO90/00735 | 7/1990 | PCT Int'l Appl. . |
| 258145 | 5/1949 | Switzerland . |
| 24848 | 4/1914 | United Kingdom . |
| 1446868 | 8/1976 | United Kingdom . |
| 2197693 | 5/1988 | United Kingdom . |

Primary Examiner—Andres Kashnikow
Assistant Examiner—Joseph A. Kaufman
Attorney, Agent, or Firm—Quarles & Brady

[57] ABSTRACT

For the manual discharge of a pulverulent medium a discharge apparatus (1) has an air pump (9), whose compressed air flow receives the powder medium via an injector (37) and a turbulence chamber (38) from a dosing mechanism (25) automatically refillable from a medium reservoir (4) and is discharged accompanied by acceleration through an outlet channel (21). Thus, with a compact construction and easy handling, the production of an aerosol for inhalation purposes or the like is ensured in simple manner.

43 Claims, 2 Drawing Sheets

MEDIA DISPENSER FOR DISPENSING A DOSED MEDIUM IN A GAS FLOW

CONTINUING DATA

This application is a continuation of Ser. No. 07/752,839; filed Aug. 30, 1991 now abandoned.

BACKGROUND OF THE INVENTION

The invention relates to a discharge apparatus for media, which is suitable for a single medium and a separately stored, identical or non-identical, flowable media, optionally having a different aggregate state, in which the medium is preferably at least partly liquid pulverulent as powdery. Appropriately, the discharge apparatus is constructed in such a way that the medium is fed or torn out of one or more medium chambers with a gas flow. The medium chamber can be formed by a medium reservoir.

Such dispensers are known as inhalers for pulverulent substances. In the latter, a powder-containing capsule is opened by destruction, and its content is sucked in with the respiratory air of the inhaling person.

Discharge apparatuses are also known in which liquid or pulverulent substances are atomized, dispersed and mixed by means of a compressed gas flow for producing an aerosol. However, the discharge apparatus must be connected to an external compressed gas source, which greatly restricts the usability thereof.

European patent application 309 010 also discloses a discharge apparatus combined with an air pump which has proved very satisfactory. However, the medium with the compressed air flow is not fed out of a chamber, and instead, the compressed air flow is merely supplied separately to a discharge nozzle, where mixing takes place; i.e., initially the medium is conveyed independently of the air flow and via a separate pump to the discharge nozzle.

OBJECTS OF THE INVENTION

An object of the invention is to provide a dispenser of the aforementioned type, which avoids the disadvantages of known constructions. Another object is to independently of external compressed gas sources ensure an effective delivery of the medium from a reservoir-like medium chamber. Further objects will be apparent from the effects and advantages described.

SUMMARY OF THE INVENTION

According to the invention, the dispenser has a manually operable device for producing the compressed gas, which can be at least partly supplied to a zone, where it receives an initially stationary medium, picks it up and then delivers it to the outside. Thus, the discharge apparatus can be used at any time; can have a very compact construction, and permits an aerosol-like discharge of varied substances with different aggregate states, particularly pharmaceutical, cosmetic and similar substances.

Appropriately, the apparatus either has an injector directed against or along a storage device for the medium or a turbulent channel, in whose vicinity it is possible to achieve, by cross-sectional constriction, relatively high gas flow turbulences and flow rates, so that the medium is picked up in very finely divided, mixed form. A compressed gas opening can be directed roughly counter to the flow direction out of said region or the medium can be supplied solely as a result of its flow characteristics via grid-like transverse channels to the area of the gas flow and can be received by the latter through vacuum in the transverse channels.

Advantageously, a dosing mechanism is provided for the medium, so that as a function of the manual actuation, only a specific medium quantity is delivered and discharged. Appropriately, the dosing mechanism is directly connected to a medium reservoir via a flow section and, apart from weight action, can also be fed into a dosing chamber in that a limited vacuum is produced in the corresponding area by the gas flow. After filling, the dosing chamber can be closed at the inlet side as a function of the operating path of the dosing mechanism, while no valve is required between the dosing chamber or medium storage device and the discharge opening leading into the open or into a mouthpiece.

As a result of the inventive construction, only a single pump is required, namely that for producing compressed air. It is also possible for several pumps, reservoirs, dosing mechanisms, injectors and associated means defined in the claims to be connected in series or in parallel.

Although other actuating movements are conceivable, the discharge apparatus is appropriately exclusively operated by a roughly linear stroke movement, and its outer end faces remote from one another can be formed by two telescopically interengaging components form the handle. One of the components can form an at least partly exposed medium reservoir, refillable by means of a closable opening, and which carries a pump piston, which engages in the other component, which defines the pump chamber. Both components are fixed to one another in simple manner by snap connections, so that a very simple construction is obtained.

BRIEF FIGURE DESCRIPTION

These and other features can be gathered from the claims, description and drawings and the individual features, either singly or in random subcombinations, can be realized in an embodiment of the invention and in other fields and can represent advantageous, independently protectable constructions, for which protection is hereby claimed. Two embodiments of the invention are described hereinafter relative to the drawings, wherein show:

FIG. 1 An inventive discharge apparatus in axial section.

FIG. 2 Another embodiment in a representation corresponding to FIG. 1.

DETAILED DESCRIPTION OF PREFERRED EXAMPLE EMBODIMENTS

Figure 1:
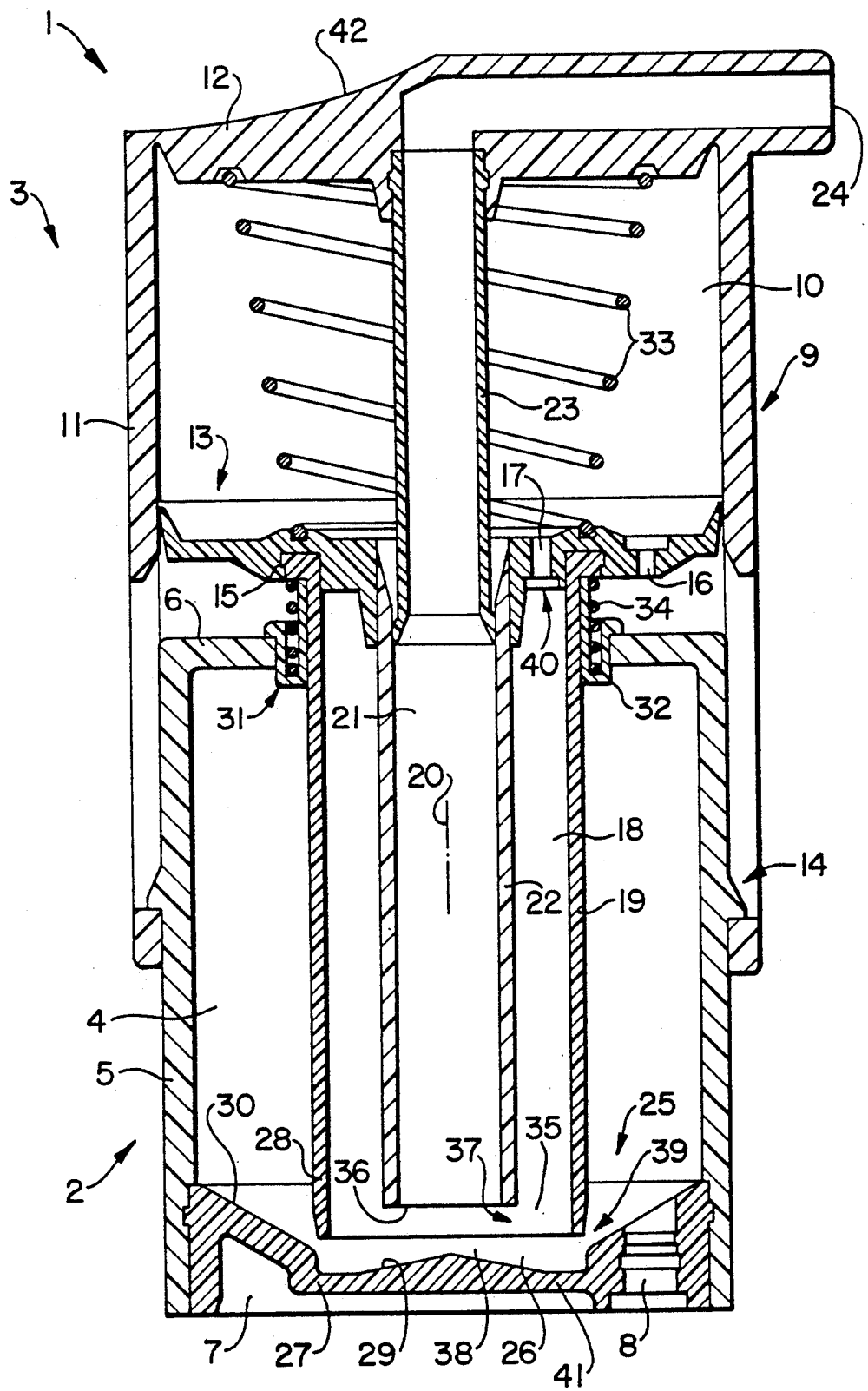

The discharge apparatus 1 only comprises two prefabricated subassemblies 2, 3 assembled by a plug connection and has a medium reservoir 4 from which is discharged during each actuating stroke a partial quantity. Another subassembly 2 forms with its outer casing or jacket 5 the external boundary of the medium reservoir 4 and the associated longitudinal portion of the discharge apparatus. A hollow body is formed by the jacket 5 with a one-piece, circular disk-like end wall 6 at one end and a substantially completely countersunk cover 7 at the other. An eccentric filling opening 8 for the medium reservoir 4, to be closed with a stopper, is provided in the snapped-in cover 5. The two subassemblies 2, 3 form the two components of a pump 9 displaceably mounted against one another by means of a pump stroke, and its pump chamber 10 is bounded by the facing ends of the two subassemblies 2 and 3 and the outer jacket 11 of the subassembly 3, into whose open end is inserted the subassembly 2. The medium reservoir 4 and pump chamber 10 are cross-sectionally circular, the internal cross-section and the external width or diameter of the pump chamber 10 being larger than that of the medium chamber 4. The jacket 11 is constructed in one piece with an end wall 12 forming the other end of the discharge apparatus 1 and receives, as the piston path, a circular pump piston 13 facing the same and which is mounted on the subassembly 2 and is directly adjacent to the end wall 6.

The two subassemblies 2, 3 are fixed against one another axially and to prevent rotation by at least one snap connection 14. Each snap connection 14 has, on the outer circumference of the jacket 5, a projecting snap cam, and for its engagement in the jacket or casing 11, an axial slot, the piston path being connected up to the end wall 12 to the axial slots. The cup-shaped pump piston 13, whose edge forms a sealing lip and which is also fixed by means of a snap connection 15, is provided radially outside its snap fastening in the bottom with at least one gas intake 16 for the pump chamber 10, which can draw in by means of the axial slots and which is provided with a not shown, spring-free check valve. Within the snap connection 15 in the bottom of the pump piston 13, at least one gas outlet 17 is provided passing through the same and by means of which, during the pump stroke, the air from the pump chamber 10 is forced downwards into a circular flow channel 18. The latter is bounded by a channel jacket 19 located within the medium reservoir 4 and bounding the inner circumference thereof and which passes through the end wall 6, and at its associated end fixes the pump piston 16 to the snap connection 15. Substantially all the aforementioned components are located in a central axis 20 of the discharge apparatus 1.

Within the flow channel 18 in contact-free manner a narrower outlet channel 21 is provided, which is bounded by two channel parts 22, 23 which are telescopically axially displaceable against one another with the subassemblies 2, 3. A channel part 22, which bounds on the inner circumference the circular flow channel 18, is fixed by one end radially within the gas outlet 17 in a central opening of the pump piston 13, and in the same way as the channel jacket 19, projects from the pump piston or the end wall 6 freely into the medium reservoir 4. The other channel part 23 guided with a sealing lip on the inner circumference of the channel part 22 is fixed by its corresponding end, and a snap connection to the end wall 12 via an end portion of the outlet channel located therein the channel part 23 leads to an outlet opening 24, which can be positioned in the axis 20 or directed at right angles thereto.

For measuring a medium charge to be discharged with one piston stroke, a dosing mechanism 25 is provided in the bottom region of the medium reservoir 4, which has a dosing chamber 26 constituted by two chamber parts 27, 28 opened and closed as a function of the pump stroke. One chamber part 27 is substantially cup-shaped and is formed by the associated end wall or the cover 7 of the medium reservoir 4. The other chamber part 28 is formed by the associated end portion of the channel jacket 19 which, up to abutment with the bottom face 29, is insertable in closely adapted manner into the jacket of the chamber part 27 and bounds with the latter in the starting position a ring slot-like transfer opening. An obtuse-angled, conical discharge hopper 30 is radially connected to the jacket or bottom surface of the chamber part 27, and its radially inner area forms one boundary of the transfer opening and by means of which the medium can flow out of the medium reservoir 4 onto the bottom surface 29. The bottom surface 29 is appropriately raised towards the center, so that the medium thereon comes to rest in a circular storage means, which is roughly congruent with the flow channel 18.

The chamber part 28 is mounted on the end wall 6 with a mounting support 31 for the channel jacket 19 so as to be displaceable axially between the closed position for the transfer opening and the starting position. An inverted jacket 32 is fixed with its radially outer jacket portion in the passage opening of the end wall 6 and with its radially inner jacket portion to the outer circumference of the end of the channel jacket 19 of the pump piston 13. The two jacket portions pass into one another via a ring portion at their ends remote from the pump piston 13 and located within the medium reservoir 4. Between the two jacket portions, a bearing spring is located on the outer circumference of the channel portion 19 and bears with one end on the ring portion of the inverted jacket 32 and can optionally constitute a restoring spring 34 for restoring the chamber part 28 to the starting position. This restoring spring 34 acting axially with its other end on the pump piston 13 is opposed by a stronger restoring spring 33, which is pretensioned between the end wall 12 and the pump piston 13 about the channel part 23 in the pump chamber 10. The restoring force acting on the chamber part 28 is at least sufficiently large to allow the opening of the dosing mechanism 25 when the restoring spring 33 is in the starting position. As a function of the matching of the two opposing restoring forces, the dosing mechanism 25 can be closed at the start of the pump stroke, or dependent on the pressure of the pump 9, only after a first part of said stroke.

The lower end of the flow channel 18 forms a circular opening 35 which is directed against the bottom surface 29 and which is bounded on the outer circumference of the chamber part 28, on an end of the depressed ring zone of the bottom surface 29 and on the inner circumference by the associated end of the channel part 22, which, when the dosing mechanism 25 is closed, faces with a gap the frustum-shaped, central region of the bottom surface 29. This end of the channel part 22 simultaneously forms a central outlet 36 for the medium to be fed out of the storage or dosing chamber 26 through the outlet channel 21 or the inlet of the outlet channel 29. As a result of the described construction, in the vicinity of the ring opening 35, which in the pump position is significantly constricted compared with the cross-sections of the ring channel 18, an injector 37 is formed with a deflection of the gas flow at the bottom surface 29 by approximately 180°. By the opening area, the closed dosing chamber and the outlet area, a turbulence chamber 38 is also formed for whirling up the medium.

Appropriately, the discharge apparatus 1 operates by the following process. The remote faces of the discharge apparatus 1 formed by the cover 7 and the end wall 12 serve as pressure handles 41, 42 for the one-handed, manual operation of the discharge apparatus. The discharge apparatus can have relatively small dimensions, namely, a diameter of less than 50 mm and a length of less than 80 mm. In the case of manual compression of the two subassemblies 2, 3, initially the cylinder jacket 11 is displaced with respect to the pump piston 13 in opposition to the tension of the restoring spring 33, so that a pressure builds up in the pump chamber 10. As a function of whether a spring-free check valve or a pretensioned pressure-relief valve as the control valve 40 is associated with the circular gas outlet 17 distributed over the flow channel 18, immediately after building up a corresponding overpressure, compressed air is fed into the flow channel 18. Beforehand, medium has trickled into the cup-shaped receptacle of the chamber part 27 from the medium reservoir 14, via the hopper 30, as a result of the manipulations which in any case occur. On reaching a first part of the pump stroke, the chamber part 28 is moved by the restoring spring 33 into the closed position. The air delivered in the meantime and while the transfer opening is becoming narrower, blows virtually all the medium away from the seat for the chamber part 28 until the transfer opening is closed and the chamber part 28 is fixed in stop-limited manner.

The further delivered air, accompanied by whirling up and deflection, carries the medium on the bottom surface 29 with it into the outlet 36, through the outlet channel 21 and outwards through the outlet opening 24. Towards the end of the pump stroke, the tension of the restoring spring 33 can rise to such an extent that the bottom of the chamber part 27 can slightly elastically deform under the pressure of the actuating force manually acting thereon, and it is in fact moved towards the outlet 36, so that, without closing, the opening 35 continuously becomes narrower and the flow rate correspondingly higher. This ensures a very effective and complete emptying of the dosing chamber. If subsequently the discharge apparatus 1 is released, accompanied by the closing of the valve 40, the pump 9 initially returns to its starting position, after which the dosing chamber 26 is again opened, so that immediately medium can flow again. Appropriately, other than the springs, at least one or substantially all the described components are made from plastic.

Figure 2:
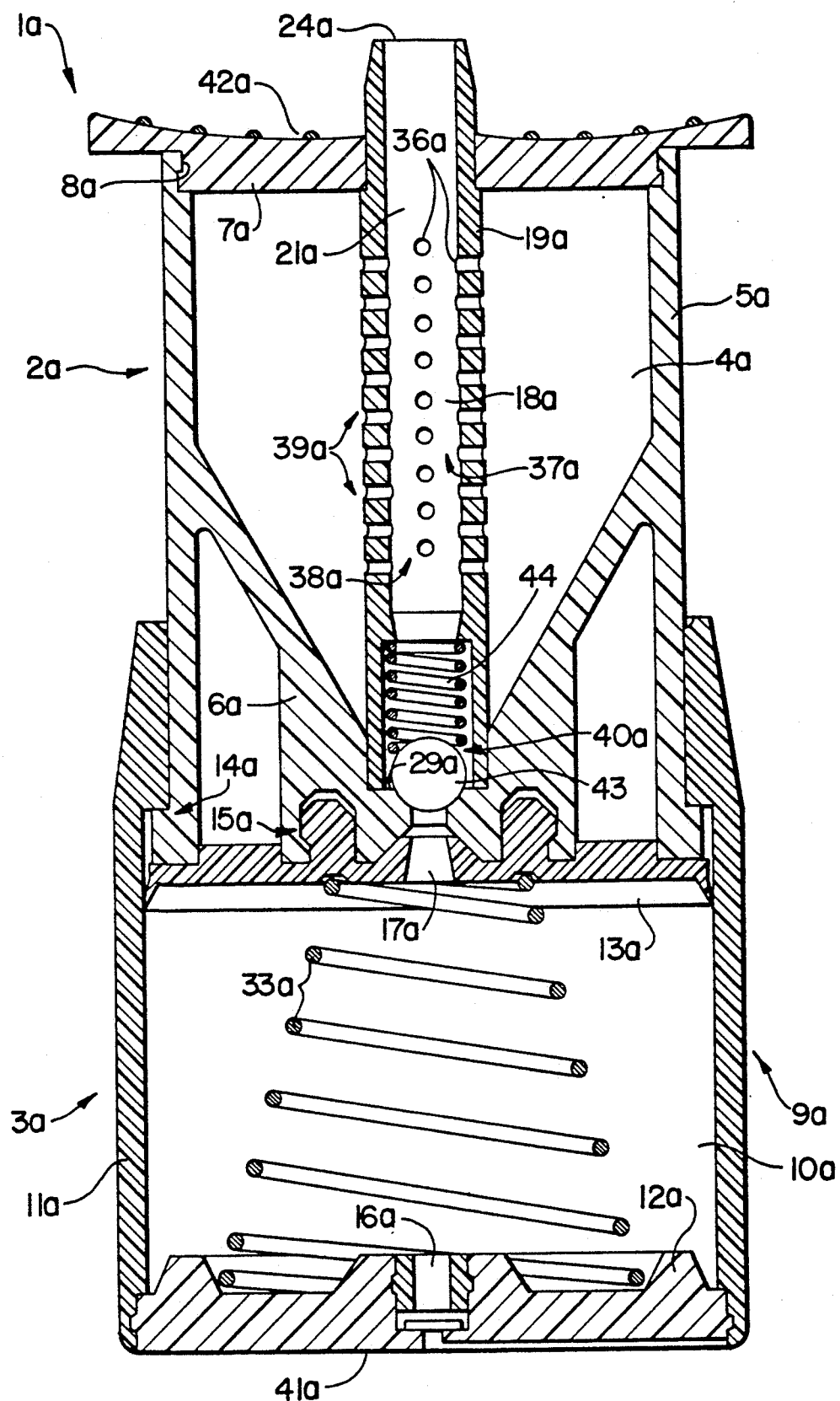

In the case of the construction according to FIG. 2, the pump *9a*is located on the end of the medium reservoir *4a* remote from the outlet opening *24a*, so that the pump chamber *10a*, does not have to be traversed by a channel. It has in the bottom wall of the pump piston 13*a* a gas outlet 17*a* directed in the discharge direction and which directly issues into one end of the substantially linear flow channel 18*a*, whose other end forms the outlet opening 24*a*. The valve 40*a* has a spherical valve body 43 located at least partly within the associated end of the flow channel 18*a* and which is spring-loaded towards the closed position with a valve spring 44 located in the flow channel 18*a*.

The channel jacket 19*a* of the flow channel 18*a* traverses the medium reservoir 4*a* and is provided with a plurality of substantially radial transverse channels 36*a* in the form of approximately linear jacket openings distributed over the circumference, and in its longitudinal direction and through these, medium can pass in finely divided form from the medium reservoir 4*a* into the flow channel 18*a*. In FIG. 1 a slide valve 39 for the medium is formed by the chamber parts 27, 28. In FIG. 2, a transfer control 39*a* is provided here and the cross-sectional shape, length, individual width and total width of the transverse channels 36*a* are adapted to the flow behavior of the medium to be discharged.

In this case, the piston 13*a* is fixed in positionally rigid manner by means of a snap connection 15*a* directly to the associated end of the casing of the medium reservoir 4*a*. The two subassemblies 2*a*, 3*a* are interconnected by means of a corresponding snap connection 14*a*. The two snap connections 14*a*, 15*a* can be provided on separate, sleeve-like telescoping jacket portions of the reservoir casing, whose space appropriately tapers in funnel-like manner towards the gas outlet 17*a*. The channel jacket 19*a* is fixed between the end walls of the medium reservoir 4*a* and traverses the cover 7*a*, which can be removed for refilling, and which in this case, is located at the end of the medium reservoir 4*a* adjacent to the outlet opening 24*a*. The pump chamber 10*a* is closed at the end remote therefrom by a corresponding, snapped-in cover 12*a*, which has the valve-controlled gas inlet 16*a*. Otherwise, in FIG. 2, corresponding parts are given the same reference numerals as in FIG. 1, but followed by a letter "a".

On operating the discharge apparatus 1*a* in the above described manner, firstly, a pressure is built up in the pump chamber 10*a* until the valve 40*a* opens. As a result, any residual medium which has sunk in ring-like manner around the valve body 43 is suddenly whirled up. As the air flow flows along the radially inner ends of the transverse channels 36*a*, medium is torn therefrom in predistributed form, further mixed by whirling up with the air flow and discharged through the outlet opening 24*a*.

Individual features, components and functions of the two embodiments can be provided together in a single embodiment.

We claim:

1. A media dispenser comprising:

means for generating a gas flow, said generation means including at least one gas path;

a medium storage reservoir;

means for separating a dosed amount of the medium from medium remaining in the reservoir and delivering the dosed amount of medium from said reservoir to the gas flow, which is guided along said at least one gas path; and means for predepositing said dosed amount of the medium in said at least one gas path and for entraining the amount with the gas flow for common discharge of the amount and the gas flow.

2. The dispenser according to claim 1, wherein said at least one medium reservoir has a deposit space separate from a medium storage of the medium reservoir, and the amount of medium is repeatedly deposited in said deposit space free of capsule encasing.

3. The dispenser according to claim 1, wherein said means for generating a gas flow is a manually operable compressed gas device (9, 9*a*), the compressed gas device being located substantially coaxial with said medium reservoir.

4. The dispenser according to claim 3, wherein said compressed gas device includes a thrust piston pump having a pump piston (13, 13*a*) directly positionally connectable to said medium reservoir (4, 4*a*).

5. The dispenser according to claim 3, wherein said gas device (9, 9*a*) has a gas chamber (10, 10*a*) which has a width extension transverse to an axial direction at least as large as a corresponding width extension of said medium reservoir (4, 4*a*).

6. The dispenser according to claim 1, wherein said gas path is formed by at least one flow channel (18, 18*a*) for the gas flow, said channel traversing said medium reservoir (4, 4*a*) at least during a part of a discharge operation, said flow channel being substantially sealingly separated from said medium reservoir.

7. The dispenser according to claim 6, wherein said at least one flow channel (18, 18a) is located substantially coaxial with said medium reservoir.

8. The dispenser according to claim 1, wherein said medium reservoir (4, 4a) is cross-sectionally substantially annular over an entire axial extension defining an annular reservoir space, said space being free of interrupting configurations.

9. The dispenser according to claim 1, further comprising at least one connecting means defined by at least one injector (37, 37a) for conveying the medium and at least one turbulence chamber (38, 28a) for the medium and wherein a compressed gas device (9, 9a) is the means for generating the gas flow and is connected to said outlet opening by at least one of said connecting means.

10. The dispenser according to claim 9, wherein said gas path includes at least one nozzle (35) which issues into at least one of said turbulence chamber (38) and said injector (37), said at least one nozzle providing an annular nozzle opening.

11. The dispenser according to claim 9, wherein said gas path includes a reception for the predeposited amount of medium and a rising outlet channel having a lower inlet, said at least one injector (37, 37a) being provided in the vicinity of said reception for the predeposited amount of medium and said inlet of said rising outlet channel (21, 21a).

12. The dispenser according to claim 9, wherein at least one injector provides a flow deflection for the gas flow and the medium to be discharged between substantially 90° and 180°.

13. The dispenser according to claim 1, wherein said gas path includes at least one flow channel (18, 18a), said flow channel having an axial extension and an annular circumferential extension, said flow channel having at least one medium inlet distributed over at least one of said annular circumferential extension and said longitudinal extension.

14. The dispenser according to claim 13, wherein upstream of said at least one medium inlet, said gas path has a control valve (40, 40a) for the gas flow which is connected to said flow channel (18, 18a).

15. The dispenser according to claim 13, wherein said flow channel is defined partly by a channel jacket, said at least one medium inlet providing at least one opening, said opening crossing said channel jacket (19a), said channel jacket separating said flow channel (18a) and said medium reservoir (4a), said at least one opening having a length extension at least equal to its width extension.

16. The dispenser according to claim 1, wherein said medium reservoir has a bottom surface and said gas path has a gas jet opening, and for predepositing at least part of the amount of medium said at least one bottom surface (29, 29a) of the medium reservoir is provided as a medium predepositing face to be covered by said at least part of the amount of medium from said medium reservoir (4, 4a), said gas jet opening (35) being directed past said predepositing face.

17. The dispenser according to claim 16, wherein said gas path has an inlet opening (36) and an outlet channel (21) for the medium, said inlet facing said predepositing face.

18. The dispenser according to claim 17, wherein said inlet opening (36) is annularly surrounded by said gas jet opening (35).

19. The dispenser according to claim 1, wherein a medium dosing mechanism (25) is provided for substantially separating the amount of medium from the medium reservoir prior to said generating means generating the gas flow and entraining the amount of medium with the gas flow.

20. The dispenser according to claim 19, wherein said medium reservoir has a bottom region and a dosing chamber (26) of said dosing mechanism (25) is at least partly located in said bottom region, said medium reservoir being connected to said dosing chamber (26) and at least partly bounded commonly with said dosing chamber (26).

21. The dispenser according to claim 1, wherein said means for generating the gas flow is a gas pump (9, 9a) having at least one pump piston (13, 13a) and at least one pump cylinder, said pump piston and said pump cylinder being substantially directly mounted on said medium reservoir (4, 4a).

22. The dispenser according to claim 1, wherein said means for generating the gas flow is a gas pump (9, 9a) having at least one pump piston (13, 13a) and at least one pump cylinder, said pump piston and said pump cylinder being mounted with at least one snap connection (14, 15 or 14a, 15a) to said medium reservoir.

23. The dispenser according to claim 1, wherein said gas path includes a flow channel (21) for the gas flow which is formed by a telescopic channel providing at least two channel parts (22, 23), telescopingly displaceable with respect to each other.

24. The dispenser according to claim 23, further comprising two handles movable against one another for activating said means for generating a gas flow and wherein said means for generating a gas flow includes a pump having a pump piston and a first one of said channel parts (22, 23) is located on said pump piston (13) and a second one of said channel parts is connected to one of said two handles (41, 42).

25. The dispenser according to claim 24, wherein said handles (41, 42) are formed by remote end walls of said medium reservoir (4) and a chamber (10) of said pump.

26. The dispenser according to claim 1, wherein said gas path includes a flow channel (21) for the gas flow which traverses at least one of spaces defined by said medium reservoir and a pump chamber (10).

27. A media dispenser comprising:

means for generating a gas flow, said generation means including at least one gas path;

a medium storage reservoir;

means for delivering the medium from said reservoir to the gas flow, which is guided along said at least one gas path; and means for separately predepositing a dosed amount of the medium in said at least one gas path and for placing the amount into the gas flow for discharge, said dispenser having an outlet opening for the discharge, wherein a medium dosing mechanism (25) is provided for substantially separating the amount of medium from the medium reservoir prior to said generating means generating the gas flow, wherein said dosing mechanism (25) provides a dosing chamber (26) defined by two chamber parts (27, 28) movable against one another between a filling and a discharge position.

28. The dispenser according to claim 27, wherein a lower chamber part (27) of said at least two chamber parts is cup-shaped.

29. The dispenser according to claim 27, wherein said medium reservoir includes a bulk medium ducting hopper and a lower one of said chamber parts (27) has an edge connected to said medium reservoir by said bulk medium ducting hopper (30).

30. The dispenser according to claim 27, wherein said gas path has a flow channel defined by an outer jacket section which forms an upper one of said chamber parts (28).

31. The dispenser according to claim 30, wherein said gas path including an outlet channel and said flow channel (18) surrounds said outlet channel (21) for the medium.

32. The dispenser according to claim 27, wherein an upper one of said chamber parts (28) is closingly insertable into a jacket of a lower one of said chamber parts (27).

33. The dispenser according to claim 27, wherein said dosing chamber has a medium inlet, said dosing chamber transferring (26) from a medium receiving position to a condition closed with respect to an inlet as a function of at least one of a medium pressure and an operational motion path.

34. The dispenser according to claim 33, wherein closing of said dosing chamber (26) is delayed with respect to compressed air delivery to said dosing chamber (26).

35. The dispenser according to claim 33, wherein said gas path is defined by a piston unit and a movable one of said chamber parts (28) of said dosing chamber (26) is located on said piston unit.

36. The dispenser according to claim 35, wherein said piston unit is a pump piston (13) and is a part of said means for generating the gas flow.

37. The dispenser according to claim 27, wherein a first one of said chamber parts (28) traverses said medium reservoir (4) at an end remote from a second one of said chamber parts (27).

38. The dispenser according to claim 27, further comprising a first spring and wherein said medium reservoir has an end wall and one of said chamber parts (28) is controlled by spring tension of said first spring and movably mounted on said end wall (6).

39. The dispenser according to claim 38, wherein said one of said chamber parts (28) is mounted with an inverted jacket (32).

40. The dispenser according to claim 38, further comprising a second spring of different spring characteristic than said first spring, said first and second springs acting in opposite directions on said chamber part (28).

41. A media dispenser comprising:
means for generating a gas flow, said generation means including at least one gas path;
a medium storage reservoir;
means for delivering the medium from said medium storage to the gas flow, which is guided along said at least one gas path; and
means for primarily separating and predepositing a dosed amount of the medium in a predepositing station of said at least one gas path and for subsequently entraining the predeposited amount of medium with the gas flow for common discharge of the predeposited amount of medium and the gas flow.

42. A media dispenser comprising:
means for generating a gas flow, said generation means including at least one gas path;
a medium storage reservoir;
means for depositing a dosed amount of the medium substantially separately from medium remaining in the reservoir and delivering the dosed amount of medium from said reservoir to the gas flow, which is guided along said at least one gas path; and
means for predepositing said dosed amount of the medium in said at least one gas path and for entraining the amount with the gas flow for common discharge of the amount and the gas flow.

43. The medium dispenser according to claim 42, further comprising wall structure separating said medium storage reservoir and said gas path, said wall structure having at least one connecting channel, wherein said means for depositing a dosed amount of the medium and delivering the dosed amount of medium from said reservoir to the gas flow operates through said connecting channel.

* * * * *